(12) United States Patent
Carnazza

(10) Patent No.: US 8,895,541 B2
(45) Date of Patent: Nov. 25, 2014

(54) METHODS FOR INHIBITING THE DEVELOPMENT OF HUNTINGTON'S DISEASE

(76) Inventor: James A. Carnazza, Holden, MA (US)

(*) Notice: Subject to any disclaimer, the term of this patent is extended or adjusted under 35 U.S.C. 154(b) by 315 days.

(21) Appl. No.: 12/961,250

(22) Filed: Dec. 6, 2010

(65) Prior Publication Data

US 2011/0077226 A1    Mar. 31, 2011

Related U.S. Application Data

(63) Continuation-in-part of application No. 12/719,361, filed on Mar. 8, 2010, now abandoned, which is a continuation of application No. 11/627,978, filed on Jan. 28, 2007, now Pat. No. 7,674,592, which is a continuation of application No. 10/654,850, filed on Sep. 4, 2003, now abandoned.

(60) Provisional application No. 60/443,397, filed on Jan. 29, 2003, provisional application No. 60/408,184, filed on Sep. 4, 2002.

(51) Int. Cl.
*A61K 31/565* (2006.01)
*A61P 25/00* (2006.01)

(52) U.S. Cl.
USPC .......................................... 514/182; 514/17.7

(58) Field of Classification Search
None
See application file for complete search history.

(56) References Cited

U.S. PATENT DOCUMENTS 7,674,592 B2    3/2010    Carnazza

OTHER PUBLICATIONS

Arrasate et al., Nature, 431:805-810, 2004.*
Penney et al. Annals of Neurol., 41: 689-692, 1997.*
Chong et al., Human Molecular Genetics, 6(2): 301-309, 1997.*
Huntington Study Group, Mov Disord., 11(2):136-142, 1996.*
Bode et al., Human Mol Genetics, 17(17):2595-2609, 2008.*
Myers RH., NeuroRx, 1:255-262, 2004.*
Strickler et al. Clin Chem Lab Med 44(7):883-887, 2006.*
Mhatre et al., Nature Genetics, 5: 184-188, 1993.*
Túnez et al. Life Sciences, 80:1221-1227, 2007.*
Túnez et al., Neurochemistry International, 48:367-373, 2006.*
Papalexi et al., Eur J Neuroscience, 22(6):1541-1546, Sep. 2005.*
Markianos et al., Ann Neurol., 57(4):520-525, Apr. 2005.*
Milewich, L., et al., "Activity of 17β-Hydroxysteroid Oxidoreductase in Tissues of the Human Fetus," *J. of Endocrinology*, 123:509-518 (1989).
Bonelli, R., et al., "A Review of the Treatment Options for Huntington's Disease," *Expert Opin. Pharmacother*. 5:767-776 (2004).
Piccioni, F., et al., "Polyglutamine Tract Expansion of the Androgen Receptor in a Motoneuronal Model of Spinal and Bulbar Muscular Atrophy," *Brain Research Bulletin* 56(3/4):215-220 (2001).
Eckert, R., Animal Physiology, pp. 314-320 (1988).
Nausieda, P., et al., "Chorea Induced by Oral Contraceptives," *Neurology* 29:1605-1609 (1979).
Ott, B., et al., "Cognitive Decline Among Female Estrogen Users in Nursing Homes," *Journals of Gerontology: Medical Sciences* 57A(9):M594-M598 (2002).
Koller, W. C., et al., "Estrogen Treatment of Dyskinetic Disorders," *Neurology* 32:547-549 (1982).
Heron, P., et al., "17β-Estradiol Protects Against Quinolinic Acid-Induced Lipid Peroxidation in the Rat Brain," *Metabolic Brain Disease* 15(4):267-274 (2000).
Bonuccelli, U., et al., "Steroid Therapy in Huntington's Disease," *Advances in Biochemical Psychopharmacology* 47:149-154 (1992).
Schneider S.A., et al., The Huntington's disease-like syndromes: what to consider in patients with a negative Huntington's disease gene test, Nature Clinical Practice Neurology, 3: 517 (2007).
Mangrella M., et al., Intensive hospital monitoring of adverse reactions to benzodiazepines and neuroleptic agents, Minerva Med. 89:293 (1998) [English Abstract Only].
Glazer W.M., Expected incidence of tardive dyskinesia associated with atypical antipsychotics, J Clin Psychiatry. 61 Suppl 4:21 (2000).
Web page: http://www.tardivedyskinesia.com/causes/neuroleptics.php (downloaded on Aug. 21, 2013).
Gitlin M., et al., Clinical Outcome Following Neuroleptic Discontinuation in Patients With Remitted Recent-Onset Schizophrenia, Am J Psychiatry 158:11 (2001).

* cited by examiner

*Primary Examiner* — Daniel E Kolker
*Assistant Examiner* — Stacey N MacFarlane
(74) *Attorney, Agent, or Firm* — Antoinette G. Giugliano; AGG Intellectual Property Law

(57) ABSTRACT

This invention relates to Huntington's disease and more specifically to methods for inhibiting the development of or treating Huntington's disease by administering estrogen, testosterone, precursors thereof or combinations thereof.

31 Claims, 4 Drawing Sheets

0= no movement, 5= completed task, (transverse the entire beam)

0= no movement, 5= completed task, (transverse the entire beam)

0= no movement, 5= completed task, (transverse the entire beam)

METHODS FOR INHIBITING THE DEVELOPMENT OF HUNTINGTON'S DISEASE

RELATED APPLICATIONS

This application is a continuation-in-part of U.S. application Ser. No. 12/719,361, filed Mar. 8, 2010, which is a continuation of U.S. application Ser. No. 11/627,978, which is a continuation of U.S. application Ser. No. 10/654,850, filed Sep. 4, 2003, now abandoned, which claims the benefit of U.S. Provisional Application No. 60/443,397, filed Jan. 29, 2003 and U.S. Provisional Application No. 60/408,184, filed Sep. 4, 2002.

The entire teachings of the above patent and applications are incorporated herein by reference.

FIELD OF THE INVENTION

The present invention relates to Huntington's Disease (HD) and trinucleotide repeat disorders. The present invention further relates to methods for treating individuals having HD, or reducing HD associated symptoms.

BACKGROUND OF THE INVENTION

Huntington's disease is a degenerative, neurological disease that is almost exclusively inherited from a parent. It is believed that about 30,000 people in the United States currently have Huntington's disease (HD) and about 150,000 are at risk of having inherited the disease from a parent. Individuals who are at risk of developing Huntington's disease inherit a mutated HD gene from a parent that codes for a protein now known as a mutated huntingtin protein. The HD gene is located on chromosome 4 and is characterized by an expanded trinucleotide repeat made up of cytosine, adenine and guanine (CAG). HD is an autosomal dominant disorder. Specifically the HD gene is located on a nonsex-linked chromosome, which means that men and women are equally at risk of inheriting the HD gene and, if the gene is inherited from just one of either parent, the inheriting individual will inevitably develop the disease.

HD is generally difficult to treat and individuals having HD suffer symptoms including brain tissue loss, weight loss, decreased cognitive ability loss of motor function, and several others. Physicians have often struggled to control and minimize these symptoms.

Accordingly, a need exists for a better understanding of HD. A further need exists for an effective treatment for HD as well as methods and compositions to reduce the symptoms associated with HD.

SUMMARY OF THE INVENTION

The present invention relates to methods of treating an individual having Huntington's Disease (HD) or a mutant HD gene having greater than or equal to about 36 CAG repeats (e.g., between about 36 and about 120 CAG repeats). The method involves selecting an individual having HD or an HD gene having greater than or equal to about 36 CAG repeats; and administering an amount of estrogen, testosterone, a precursor thereof, or a combination thereof. In an embodiment, estrogen is administered to a female in an amount that ranges from about 0.025 mg to about 10 mg, and testosterone is administered to a male in an amount that ranges from about 1 mg to about 35 g. The "estrogen/testosterone compound" as referred to herein is intended to mean "estrogen, a precursor thereof, or a combination thereof" when administered to a female individual and "testosterone, a precursor thereof, or a combination thereof" when administered to a male individual. The method can further include, in an aspect, measuring levels of estrogen, testosterone, a precursor thereof, or a combination thereof in the individual e.g., before administration. In this case, the amount of the administration of the estrogen/testosterone compound is sufficient to maintain certain levels of the compound in individuals with HD, especially in cases in which the levels decrease as the disease progresses. The levels to be maintained are those that are homeostatic levels of estrogen or testosterone in individuals normally associated with a 20-25 year old population. In women, a homeostatic level of an average amount of estrogen in a 20-25 year old female ranges between about 100 pg/ml and about 185 pg/ml. Homeostatic levels in male individuals of free testosterone is between about 20 pg/ml and about 40 pg/ml, and total testosterone is between 300 ng/dL and about 900 ng/dL. The method of treatment further includes reducing one or more symptoms of HD e.g., weight loss, loss of fine or gross motor function, a loss in cognitive function, chorea, loss of brain tissue or a combination thereof. One or more symptoms are reduced e.g., by a range between about 5% and about 100%. The methods of the present invention includes assessing the presence or absence of a mutant HD gene having between about 36 and 120 CAG repeats (e.g., using a DNA test, PCR testing, as further described herein).

The present invention also pertains to methods for reducing one or more symptoms associated with HD in an individual, wherein the method includes selecting an individual having HD; and administering an amount of estrogen, precursors thereof, or a combination thereof to a female, wherein the amount ranges from about 0.025 mg to about 10 mg or administering an amount of testosterone, precursors thereof, or a combination thereof to a male, wherein the amount ranges from about 1 mg to about 35 g; wherein one or more symptoms associated with HD in the individual is reduced, as compared to an individual with HD not subjected to the estrogen/testosterone compound.

The present invention further embodies preventing weight loss, or reducing the amount of weight loss in an individual having HD, by selecting an individual having HD; and administering an amount of estrogen to a female, precursors thereof, or a combination thereof, wherein the amount of estrogen ranges from about 0.025 mg to about 10 mg, and administering an amount of testosterone to a male, wherein the amount of testosterone ranges from about 1 mg to about 35 g. Such administration prevents weight loss or reduces the amount of weight loss in the individual with HD, as compared to an individual with HD not subjected to such administration. In an embodiment, the amount of weight loss is reduced by between about 5% and about 100%. In an aspect, the methods of the present invention involves selecting an individual having HD by assessing an individual for the presence or absence of a mutant huntingtin protein having a polyglutamine tract, or mutant HD gene having a CAG repeat.

Yet the present invention further relates to methods for treating an individual having HD, by assessing an individual for the presence or absence of HD or the presence or absence of a HD gene having between about 36 CAG repeats and about 120 CAG repeats; assessing one or more levels of estrogen, testosterone, precursors thereof, or a combination there in the individual; and administering an amount of estrogen, testosterone, or a combination thereof to the individual to maintain estrogen at an average level in a female individual between about 100 pg/ml and about 185 pg/ml; or in a male individual to maintain a level of free testosterone is between about 20 pg/ml and about 40 pg/ml, and/or of total testosterone is between 300 ng/dL and about 900 ng/dL. The estrogen, testosterone, or a combination thereof can be administered, for example, periodically, daily, or weekly.

The present invention also pertains to methods of treating an individual having a trinucleotide repeat disorder by selecting an individual having a trinucleotide repeat disorder; and administering to a female individual an amount of estrogen, precursors thereof or a combination thereof; or administering to a male individual an amount of testosterone, precursors thereof or a combination thereof; wherein the individual having a trinucleotide repeat disorder is treated. Examples of trinucleotide repeat disorder includes HD, Dentatorubropallidoluysian atrophy, Kennedy disease, Spinocerebellar ataxia (SA) Type 1, SA Type 2, SA Type 3, SA Type 6, SA Type 7, and SA Type 17.

Additionally, methods of inhibiting a mutant huntingtin protein in an individual having HD is also encompassed the present invention. Such methods include administering to a female individual an amount of estrogen, precursors thereof or a combination thereof; or administering to a male individual an amount of testosterone, precursors thereof or a combination thereof; wherein the mutant huntingtin protein is inhibited. In an embodiment, estrogen binds the mutant huntingtin protein and inhibits its function.

Furthermore, a method of the present invention for inhibiting the development of Huntington's disease in an individual who is at risk of developing the disease, includes some or a combination of the following steps: determining that the individual exhibits a trinucleotide repeat pattern, consisting of cytosine, adenine, and guanine, is of sufficient number to indicate a risk for developing HD; establishing that a serum level, of a preselected hormone in the individual is below normal; administering one or more hormones, selected from a group consisting of estrogen, testosterone, their respective precursors, and esters of estrogen, testosterone, and their respective precursors, in amounts sufficient to inhibit development of the disease (e.g., at a level of estrogen in women or testosterone in men comparable to that of a 20-25 year old population), wherein the individual, in an embodiment, exhibits an expanded trinucleotide repeat pattern greater than 36. In an embodiment, the individual exhibits repeats higher than 38 including expanded trinucleotide repeat patterns equal to or greater than 43 or even equal to or greater than 63. In an aspect, the individual exhibits a mutated huntingtin polyglutamine protein comprising greater than 38 glutamines. To establish that an individual's serum level is below normal, the method includes, in an embodiment, the step of testing the individual's blood sample by a suitable method such as a polymerase chain reaction.

The method of the present invention further includes, in an embodiment, the step of predetermining the rate at which one or more of the hormones binds to a polyglutamine located at an end of said huntingtin polyglutamine protein to determine a time to begin said administering step and said sufficient amount of said one or more hormones, wherein said predetermining step comprises the steps of, obtaining one or more samples of a huntingtin polyglutamine protein with known numbers of glutamines; mixing said sample with a labeled estradiol source and a buffering solution; measuring the binding affinity of the labeled estradiol source to the huntingtin polyglutamine protein. In an aspect, the binding affinity is preferably measured with a gamma counter and is equal to or less than about 50,000 counts per minute.

Another method for determining a time for administering a hormone treatment to inhibit the development of Huntington's disease in an individual who is at risk of developing the disease, generally includes the steps of: determining a plurality of binding affinities of estradiol to a mutant huntingtin polyglutamine protein with known numbers of glutamines; and measuring the serum level of hormone in said individual to determine if said serum level is below normal. In an aspect, the affinity can be measured with a gamma counter and typically is equal to or less than about 50,000 counts per minute and may be equal to or less than about 40,000 counts per minute. The mixing step may further comprise mixing said labeled hormone source with a buffering solution.

The present invention has numerous advantages. The present invention provides for an effective treatment for HD. Particularly, the methods of the present invention allow for a reduction in symptoms associated with HD. Unexplained weight loss is a tell-tale sign of HD and generally gets more pronounced as the disease progresses. For example, most HD patients consume approximately 2,000-4,000 calories/day, which is more than twice the recommended amount and still lose weight. The methods of the present invention surprisingly and significantly reduce this remarkable weight loss experienced by an individual with HD.

DETAILED DESCRIPTION OF THE INVENTION

Figure 1:
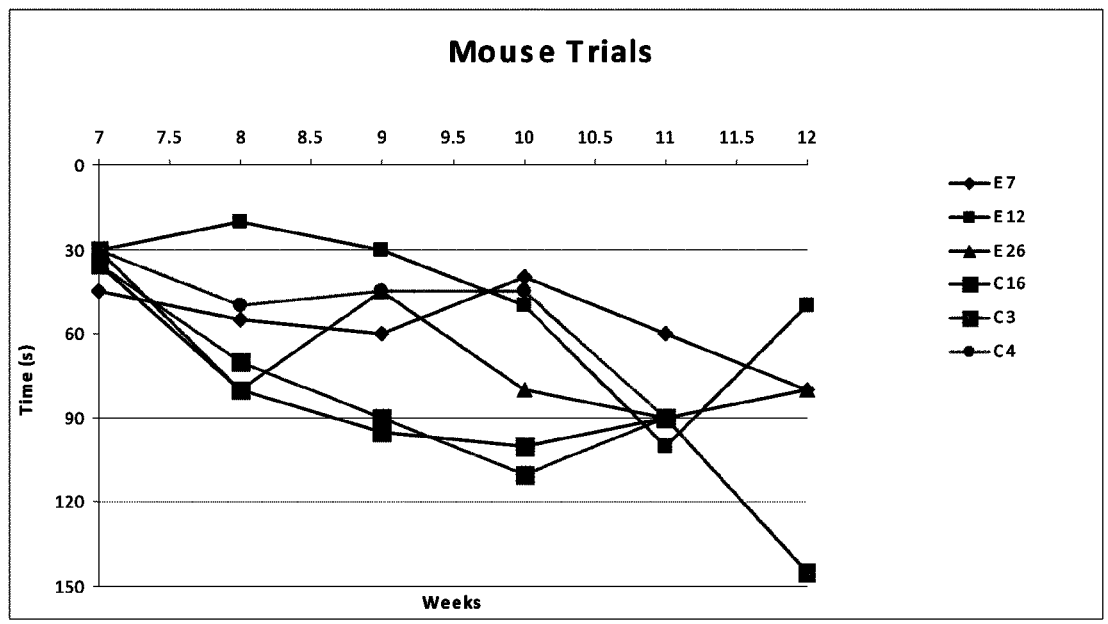
FIG. 1 is a graph showing the amount of time (in seconds) animals from groups E7, E12, E26, C16, C3 and C4 were able to traverse a ½ in beam at a certain time (in weeks).
Figure 2A:
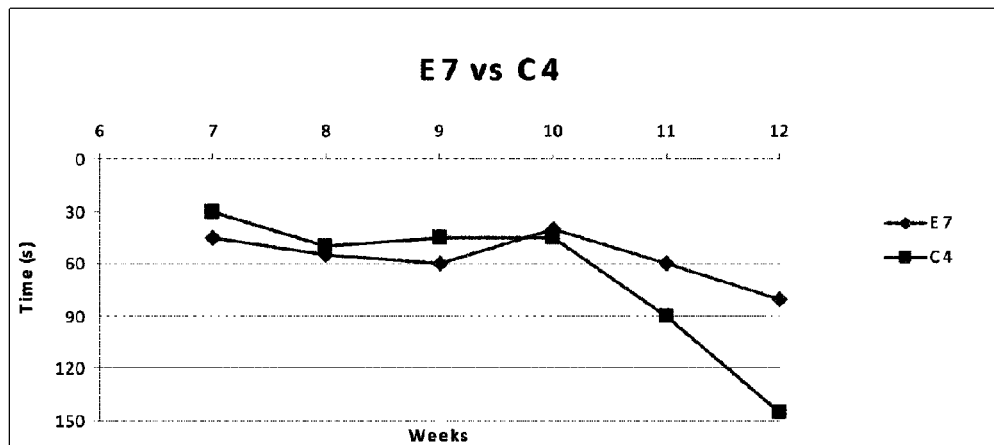
FIG. 2A is a graph showing the amount of time (in seconds) animals from groups E7 and C4 were able to traverse a ½ in beam at a certain time (in weeks).
Figure 2B:
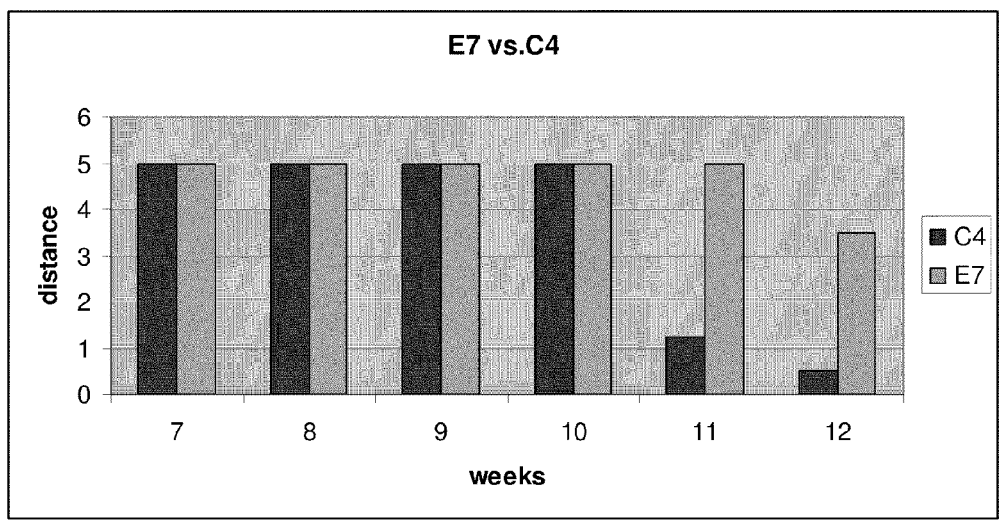
FIG. 2B is a bar graph showing the extent (0=no movement, 5=completed task, (transverse the entire beam) animals from groups E7 and C4 were able to traverse a ½ in beam at a certain time (in weeks).
Figure 3A:
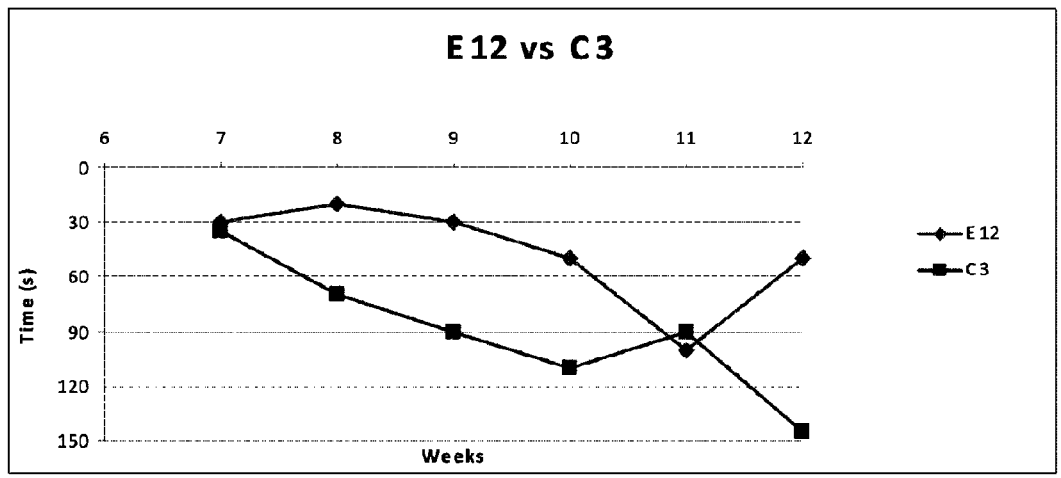
FIG. 3A is a graph showing the amount of time (in seconds) animals from groups E12 and C3 were able to traverse a ½ in beam at a certain time (in weeks).
Figure 3B:
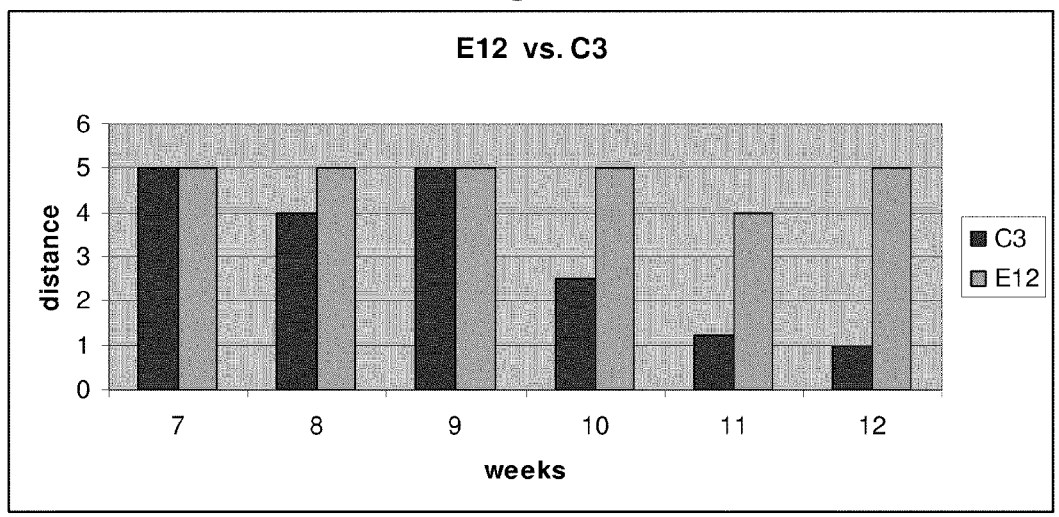
FIG. 3B is a bar graph showing the extent (0=no movement, 5=completed task, (transverse the entire beam) animals from groups E12 and C3 were able to traverse a ½ in beam at a certain time (in weeks).
Figure 4A:
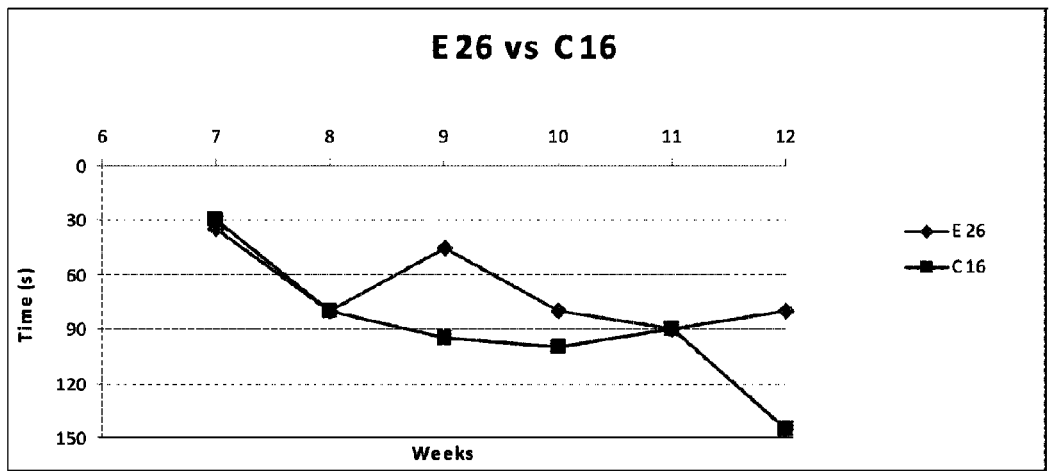
FIG. 4A is a graph showing the amount of time (in seconds) animals from groups E26 and C16 were able to traverse a ½ in beam at a certain time (in weeks).
Figure 4B:
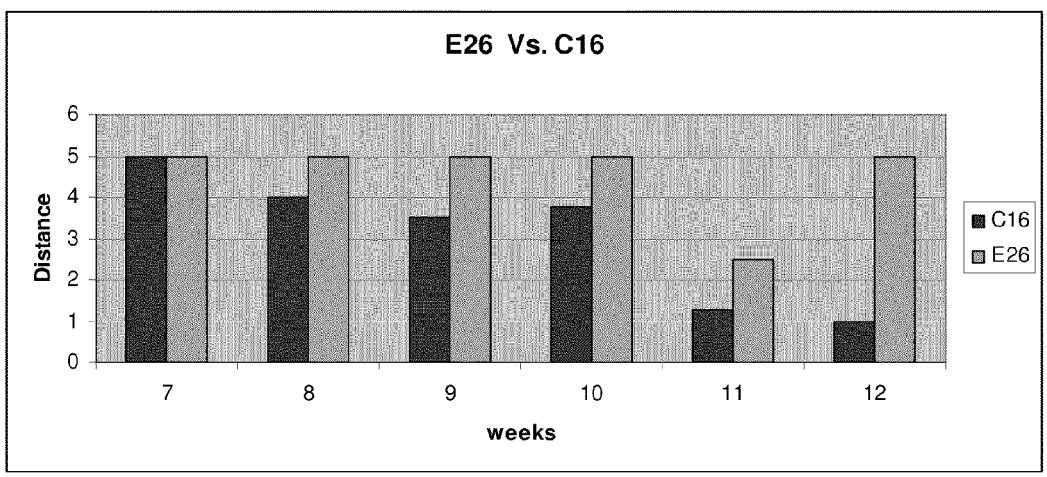
FIG. 4B is a bar graph showing the extent (0=no movement, 5=completed task, (transverse the entire beam) animals from groups E26 and C16 were able to traverse a ½ in beam at a certain time (in weeks).

A description of preferred embodiments of the invention follows.

The present invention relates to methods for testing for and inhibiting the development of Huntington's disease (HD) in individuals by administering an amount of estrogen (e.g., Estradiol), testosterone, a precursor thereof, or a combination thereof (referred herein collectively as "estrogen/testosterone administration"). In particular, the present invention relates to treating and/or preventing HD in an individual by estrogen/testosterone administration. The "estrogen/testosterone compound" as referred to herein is intended to mean "estrogen, a precursor thereof, or a combination thereof" when administered to a female individual and "testosterone, a precursor thereof, or a combination thereof" when administered to a male individual. To treat an individual with HD disease or a trinucleotide repeat disorder means to alleviate, ameliorate or reduce the severity of one or more of HD symptoms. Prevention of HD or trinucleotide repeat disorder refers to delaying or suppressing the onset of the one or more symptoms of HD. Additionally, the present invention encompasses reducing the severity of one or more HD symptoms, which refers to minimizing the extent of one or more HD symptoms that are experienced by the individual.

In an embodiment, the methods of the present invention utilize balanced hormone treatment, including estrogen, testosterone, their precursors such as DHEA and progesterone; and their esters to inhibit and/or treat HD. Accordingly, the present invention involves assessing the levels of estrogen, testosterone, precursors thereof and/or a combination thereof, and administering an amount of estrogen (e.g., Estradiol), testosterone, precursors thereof, or a combination thereof to bring one or more levels to a desired amount or within a normal range, as further described herein.

As demonstrated by the data in the Exemplification section, one of the most significant symptoms of HD in humans is the continued loss of body weight even at extreme caloric intake. In generally, individuals suffering from HD routinely continue to lose weight as the disease progresses even at 4000-5000 calorie/day intake. Along with the extreme weight loss, brain and motor function abnormalities occur, as further described herein. Individuals with HD have cognitive function, motor function and gait that are extremely impaired. Additionally HD individuals are often associated as having mood swings and outburst of rage.

Generally, HD is characterized by a trinucleotide repeat or a CAG repeat that is also further described herein. An individual having HD typically has greater than or equal to 36 CAG repeats. The mouse model used in the data of the Exemplification utilizes severely diseased mice that have an average of about 159.6 CAG repeats and demonstrate the same abnormalities as individuals having HD. Extreme weight loss during progression of the disease was observed. Cognitive inabilities in decision making, and tremendous hesitation (obsessive compulsive behavior) as well as elliptic seizure occurred in non-treated mice (i.e., the control). Some aggressive cage behavior was observed with the control animals. The data show that administration of either estrogen and or testosterone, surprisingly, abolished or greatly reduced these symptoms in severely affected HD mice. As the disease state progressed, the untreated animals displayed symptomatic abnormalities, including extreme weight loss (up to 30% Males, 28% Females). Untreated mice were not able to perform certain cognitive and motor functions such as deciding to cross a beam (impaired cognition) and demonstrated inability to traverse a beam to a safety platform once placed on it. The treated animal showed a remarkable improvement over the control animals in their ability to transverse the ½ inch beam in the allotted time frame. They demonstrated cognitive ability and showed little hesitation in deciding to cross. Once moving along the beam, the treated animals were able to control their forelimb and hind limb coordination to show little or no impairment. Cognitive and motor ability in the treated mice continued for a significant amount of time after the untreated mice were unable to traverse the beam. As described in the Exemplification, treated mice traversed the beam two to two and a half weeks after the control animals were unable to move on the beam (a 16.6% improvement over the time course of the study).

The data of the Exemplification also shows that the treated animals showed a marked improvement in weight retention, a symptom that is strongly associated with HD progression. Aziz, N. Ahmad, et al., *JON* 3062: 1872-1878 (January 2009). Also, transgenic for severe disease, the treated mice's overall weight loss was only a fraction of the untreated animal, e.g., at as little as 11% for males and as little as 9% for females. As compared to untreated mice, a significant improvement in weight loss was seen.

Taken together, these data show that the administration of estrogen and or testosterone is protective against Huntington's disease and symptoms associated with the disease. This protection is effective at more than one dose level and is shown to be quantitative in at least four areas of measurement: (1) weight loss, (2) cognitive function, (3) motor function coordination and (4) brain weight assessment. The present invention provides an effective therapy for HD.

In general, HD is a genetic, neurodegenerative disease and affects muscle coordination and certain cognitive functions. HD is characterized, in part, by neural degeneration specific to the spiny neuron in the striatum. The disease, which is characterized by an expanded CAG (cytosine-adenine-guanine), a polyglutamine repeat, often manifests itself with aging and is associated with the onset of HD. The HD gene, also referred to as the HTT gene, is located on the short arm of chromosome 4 at 4p16.3 and codes for huntingtin protein. CAG is the genetic code for the amino acid, glutamine, so a series of them results in the production of a chain of glutamine known as a polyglutamine tract (or polyQ tract). The mutant form of the huntingtin protein having an expanded polyQ tract greater than 36 Q causes HD. The present invention involves individuals having HD and/or those having an HD gene with greater than or equal to about 36 CAG repeats (e.g., about 40, 45, 50, 55, 60, 65, 70, 75, 80, 85, 90, 95, 100, 110, or 120 CAG repeats).

Symptoms of HD include psychomotor related symptoms, such as chorea, which refers to jerky, random, or uncontrollable movements. As the disorder progresses, psychomotor symptoms also include rigidity, writhing motions or abnormal posturing. Often, assessment of motor function can be done by observing the individual's walk, posture, movement and/or gait. One of skill in the art or a healthcare provider can assess such HD symptoms using methods and techniques known in the art.

A common and important symptom of HD includes weight loss. This is an important and widely accepted indicator of HD. In fact, unintended weight loss frequently complicates the course of neurodegenerative disorders and can contribute substantially to morbidity and mortality. Aziz, N. Ahmad, et al., *JON* 3062: 1872-1878 (January 2009). In fact, studies have also shown that weight loss in individuals with HD correlates with CAG repeat length. Aziz, N. A. et al., *Neurology* 71:1506-1513 (2008). An increase in weight loss was observed in individuals with high number of CAG repeats. Accordingly, the present invention relates to preventing or treating weight loss in an individual having HD and/or an increase number of CAG repeats by administering estrogen, testosterone, precursors thereof or a combination thereof. The data show that administration of estrogen or testosterone prevents weight lost with HD and increases quality of life, as further described herein. Weight loss can measured using a scale.

Seizures are also a common symptom of this form of HD. Brain tissue loss, memory loss and psychiatric symptoms including depression and anxiety are also observed. Mutant huntingtin is expressed throughout the body and associated with abnormalities in peripheral tissues that are directly caused by such expression outside the brain. These abnormalities include muscle atrophy, cardiac failure, impaired glucose tolerance, osteoporosis and testicular atrophy.

The present invention involves selecting an individual with HD and/or an individual with the mutant HD gene having greater than or equal to about 36 CAG repeats. Selecting these individuals can be done in several ways. HD can be assessed clinically by assessing components of the Unified Huntington's Disease Rating Scale (UHDRS). *Movement Disorders* (vol. 11:136-142, 1996) and *Neurology* (54:452-458, 2000). UHDRS is generally divided into four components: motor performance, cognition, behavior and functional capacity. In particular, the following items are rated: Ocular Pursuit (horizontal, vertical), Saccade Initiation (horizontal, vertical), Saccade Velocity (horizontal, vertical), Dysarthria, Tongue Protrusion, Finger Taps (right, left), Pronate/Supinate (right, left), Fist-Hand-Palm Sequence, Rigidity-arms (right, left), Bradykinesia, Maximal Dystonia (trunk, RUE, LUE, RLE, LLE), Maximal Chorea (Face, BOL, Trunk, RUE, LUE, LLE, RLE), Gait and Tandem Walking. Each item is assigned a grade from 0 to 4, and added up to quantify the progression of HD symptoms. A rating of an abnormal gate to a severely abnormal gate indicates progression of HD in the individual. The present invention includes methods for preventing the UHDRS score from worsening, as compared to the UHDRS prior to administration. Additionally, the present invention includes methods for maintaining the UHDRS score or reducing the progression of HD as measured by UHDRS, as compared to an individual with HD that is not subject to estrogen/testosterone administration. Brain tissue loss can be assessed with a head CT scan, head MRI scan, a PET scan, or other imaging techniques.

An individual can be genetically tested for the mutant HD gene and the number of CAG repeats, a test that indicates the presence or absence of HD in an individual. CAG repeats can be assessed using e.g., a PCR assay. Mangiarini et al, 1996. Briefly, a sample from the individual can be taken and assessed. The sample can be prepared using the methods known in the art. The DNA from the sample is prepared and southern blots and hybridization assays can be done for this assessment. CAG repeats can be sized by PCR using labeled primers. A polymerase (e.g., Taq polymerase) can be used along with cycling conditions (e.g., 90" @ 90° C., 25×(30" @ 94° C., 30" @ 65° C., 90" @ 72° C.), 10' @ 72° C.). PCR products can be sized using sequences and genotyping software. The PCR products from an HD affected individual can be analyzed by DNA sequencing techniques to determine the absolute number of CAG repeats. Additional methods known in the art can assess the presence of the mutant HD gene, and/or the size or length of the CAG repeat. Furthermore, DNA tests for HD disease or other trinucleotide repeat disorders can be done e.g., through targeted mutational analysis using a number of laboratories that are commercially available. In an embodiment, an individual predisposed to HD having tested positive for the expanded CAG repeats but prior to having symptoms can be selected for administration of estrogen, testosterone or both, as described herein. Alternatively, one can assess the presence of the polyglutamine tract protein or nucleic acid using methods known in the art or later developed.

HD is one of several trinucleotide repeat disorders which are caused by the length of a repeated section of a gene exceeding a normal range. Accordingly, in addition to treating HD, the present invention relates to treating diseases characterized by a polyglutamin tract or CAG repeats (e.g., greater than or equal to 36 CAG repeats), as described herein. Such polyglutamine diseases include Dentatorubropallidoluysian atrophy (e.g., about 49-88 CAG repeats), Kennedy disease (e.g., about 38-62 CAG repeats), Spinocerebellar ataxia Type 1 (e.g., about 49-88 CAG repeats), Type 2 (e.g., about 33-77 CAG repeats), Type 3 (e.g., about 55-86 CAG repeats), Type 6 (e.g., about 21-30 CAG repeats), Type 7 (e.g., about 38-120 CAG repeats), and Type 17 (e.g., about 47-63 CAG repeats).

Accordingly, an individual with a trinucleotide repeat disorder is selected with a DNA test that assesses the presence of an expanded CAG repeats, or a test that assesses the presence of the poly Q tract. Individuals can also exhibit other symptoms described herein and the progression of those symptoms, especially weight loss, indicates the progression of the disease. Estrogen/testosterone administration, prevents one or more of the symptoms described herein from worsening, or reduces the severity of the symptom by at least about 5%, (e.g., 10%, 20%, 30%, 40%, 50%, 60%, 70%, 80%, or 90%), as compared to the level of severity of the symptom just prior to administration, or as compared to an individual with the trinucleotide repeat disorder that is not subject to estrogen/testosterone administration. In another embodiment, the estrogen/testosterone administration ameliorates or improves one or more symptoms described herein by about 5%, (e.g., 10%, 20%, 30%, 40%, 50%, 60%, 70%, 80%, or 90%).

Modes and Manner of Administration, Dosages

"Estrogen/testosterone administration" refers to administering one or more of the following: estrogen, testosterone, a precursor thereof, or a combination thereof. As referred to herein, estrogen, a precursor thereof or a combination thereof is generally administered to a female individual, and testosterone, a precursor thereof or a combination thereof is administered to a male individual. Estrogen refers to a group of steroidal based compounds involved in the estrous cycle. Examples of steroidal hormone compounds that can be used with the present invention include testosterone (17beta-hydroxy-4-androsten-3-one), estrone (E1, 3-hydroxy-1,3,5 (10)-estratrien-17-one), estradiol (E2, 1,3,5(10)-estratriene-3,17beta-diol), estriol (E3, 1,3,5(10)-estratriene-3,16alpha, 17beta-triol), and progesterone (e.g., P4 (pregn-4-ene-3,20-dione)). Several of these compounds are commercially available for other purposes, such as menopause or hypogonadism-testicular failure.

The composition of testosterone is as follows:

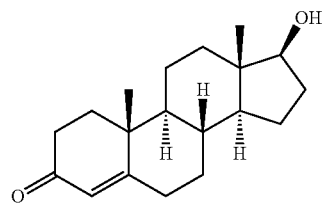

Testosterone

Similarly, the composition of estradiol includes:

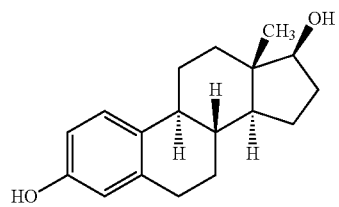

Estradiol Composition.

Estrogen compounds now known or later discovered or developed can be used with the present invention.

Estradiol comes in the form of oral, transdermal, topical, injectable, and vaginal preparations. In certain aspects, the estradiol molecule can be linked to an alkyl group at C3 position to facilitate the administration. Examples of such compounds include estradiol acetate (oral and vaginal applications), estradiol cyprionate (injectable), ethinylestradiol (oral).

In particular, a form of estradiol that can be used with the present invention is estradiol cypioate, which marketed under the name DEPO-Estradiol by Pfizer, Inc. DEPO-Estradiol contains an oil soluble ester of estradiol 17β. The chemical name for estradiol cypionate is estradiol 17-cyclopentanepropionate. DEPO-Estradiol, in an embodiment is administered intramuscularly by injection. In an embodiment, each mL contains: 5 mg/mL, 5 mg estradiol cypionate, 5.4 mg chlorobutanol anhydrous (chloral derivative) added as preservative; in 913 mg cottonseed oil. The composition of estradiol cypioate is as follows:

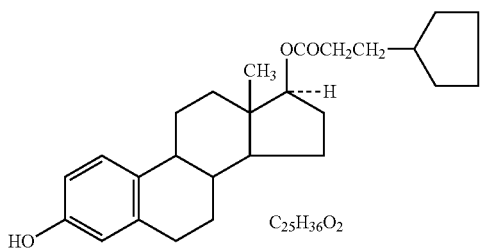

Estradiol Cypioate marketed DEPO-Estradiol™.

Similarly, a form of testosterone includes DEPO-Testosterone and can be used with the administration in the present invention. In this embodiment, DEPO-Testosterone is for intramuscular injection and contains testosterone cypionate which is the oil-soluble 17 (beta)-cyclopentylpropionate ester of the androgenic hormone testosterone. Testosterone cypionate is a white or creamy white crystalline powder, odorless or nearly so and stable in air. It is insoluble in water, freely soluble in alcohol, chloroform, dioxane, ether, and soluble in vegetable oils. The chemical name for testosterone cypionate is androst-4-en-3-one, 17-(3-cyclopentyl-1-oxopropoxy)-, (17β)-. Its molecular formula is C27H40O3, and the molecular weight 412.61. DEPO-Testosterone is commercially available in two amounts by Pfizer, Inc.: 100 mg/mL and 200 mg/mL testosterone cypionate.

The structural formula is represented below:

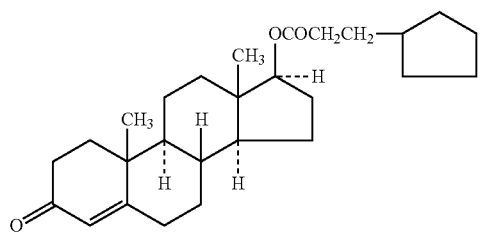

testosterone marketed as DEPO-Testosterone™.

The estrogen, testosterone, precursors thereof, or combinations thereof used in the present invention can be administered with or without a carrier. The terms "pharmaceutically acceptable carrier" or a "carrier" refer to any generally acceptable excipient or drug delivery composition that is relatively inert and non-toxic. Exemplary carriers include sterile water, salt solutions (such as Ringer's solution), alcohols, gelatin, talc, viscous paraffin, fatty acid esters, hydroxymethylcellulose, polyvinyl pyrolidone, calcium carbonate, carbohydrates (such as lactose, sucrose, dextrose, mannose, albumin, starch, cellulose, silica gel, polyethylene glycol (PEG), dried skim milk, rice flour, magnesium stearate, and the like. Suitable formulations and additional carriers are described in Remington's Pharmaceutical Sciences, (17th Ed., Mack Pub. Co., Easton, Pa.). Such preparations can be sterilized and, if desired, mixed with auxiliary agents, e.g., lubricants, preservatives, stabilizers, wetting agents, emulsifiers, salts for influencing osmotic pressure, buffers, coloring, preservatives and/or aromatic substances and the like which do not deleteriously react with the active compounds. Typical preservatives can include; potassium sorbate, sodium metabisulfite, methyl paraben, propyl paraben, thimerosal, chloral derivative, etc. The compositions can also be combined where desired with other substances used to treat HD disease or trinucleotide repeat disorders, e.g., tetrabenazin neuroleptics medications, benzodiazepines, selective serotonin reuptake inhibitors, and mirtazapine. A carrier (e.g., a pharmaceutically acceptable carrier) is preferred, but not necessary to administer the compound.

The estrogen/testosterone compound can be a liquid solution, suspension, emulsion, tablet, pill, gel, capsule, sustained release formulation, or powder. The method of administration can dictate how the composition will be formulated. For example, the composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

The estrogen/testosterone compound used in the invention can be administered intravenously, parenterally, intramuscularly (e.g., DEPO-Estradiol, DEPO-Testosterone), subcutaneously, orally (e.g., Cenestin, Estinyl, Estrace, Menest, Ogen, Premarin), nasally, topically (e.g., Estrace, Ogen, Ortho Dienestrol, Premarin, Androgel, Estrogel, Testim), by inhalation, by implant (temporarily, e.g., Estring, Femring), by injection (e.g., Testostérone Cypionate), by suppository (e.g., Vagifem) or transdermally (e.g., Androderm, Alora, Climara, Esclim, Estraderm, Vivelle, Vivelle-Dot). For testosterone administration, in an embodiment, DEPO-testosterone can be administered in amounts of 40 mg/week intramuscularly. Androgel is a gel that is applied topically twice per day in an amount of 5 gm/day or 35 gm per week. For estrogen administration, in an embodiment, Estrogel is administered once a day in an amount of 0.75 mg/day or 5.25 mg/week, whereas Vivelle-Dot is a patch that administered 0.025 mg/day or 0.175 mg/week. The composition can be administered in a single dose or in more than one dose over a period of time to confer the desired effect (e.g., periodically, daily, weekly, monthly, yearly, etc.). In one embodiment, estrogen, a precursor thereof or metabolite thereof can be administered in an amount between about 0.025 mg to about 10 mg. Such administration, according the present invention, brings the average levels of estrogen in an female individual with HD to homeostatic levels of between about 100 pg/ml and about 185 pg/ml. In another embodiment, testosterone, a precursor thereof or a metabolite there can be administered in an amount that ranges between about 1 mg and about 35 g. Such administration allows for homeostatic levels in male individuals with HD to be as follows: free testosterone is between about 20 pg/ml and about 40 pg/ml, and total testosterone is between about 300 ng/dL and about 900 ng/dL.

The actual effective amounts of compound or drug can vary according to the specific composition being utilized, the mode of administration and the age, weight and condition of the patient. For example, as used herein, an effective amount of the drug is an amount which reduces one or more HD symptoms. Dosages for a particular individual patient can be determined by one of ordinary skill in the art using conventional considerations, (e.g. by means of an appropriate, conventional pharmacological protocol).

For enteral or mucosal application (including via oral and nasal mucosa), particularly suitable are tablets, liquids, drops, suppositories or capsules. A syrup, elixir or the like can be used wherein a sweetened vehicle is employed. Liposomes, microspheres, and microcapsules are available and can be used.

For parenteral application, particularly suitable are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-polyoxypropylene block polymers, and the like. Ampules are convenient unit dosages.

The administration of a first estrogen/testosterone compound and a second estrogen/testosterone compound or compound for treating trinucleotide repeat disorders can occur simultaneously or sequentially in time. The estrogen/testosterone compound can be administered before, after or at the same time as a second compound. Thus, the term "co-administration" is used herein to mean that the first estrogen/testosterone compound and a second compound will be administered at times to achieve a reduction in symptoms, or treatment of HD or the trinucleotide repeat disorder. The methods of the present invention are not limited to the sequence in which the compounds are administered; so long as the estrogen/testosterone compound is administered close enough in time to produce the desired effect.

As hormones such as estrogen, testosterone, and their precursors decline, the protective effect of these hormones is lost and the HD disease process advances undeterred. Specifically, for example, estrogen declines by 50% in women by approximately 50 years of age and a further 80% following menopause. In an aspect, testosterone's and estrogen's, and their precursors', effects on brain functions include, but are not necessarily limited to, stimulation of the growth of the dendritic spines on spiny neurons and regulation of dopomenergic, serotonergic, adrenergic and glutamatergic functions. Testosterone, estrogen, and their precursors also increase the synthesis of certain monoamine neurotransmitters, inhibit their degradation, and interact with neurotrophins that stimulate neural growth and survival.

In an embodiment, a hormonal level of estrogen to be maintained in a women ranges between about 100 pg/ml and about 185 pg/ml. With respect to men, free testosterone levels can be maintained in a range between about 20 pg/ml and about 40 pg/ml, total testosterone levels can be maintained in a range between 300 ng/dL and about 900 ng/dL, or both. The level of estradiol can be determined by taking an E2 test, and the level of testosterone can be determined by taking a serum testosterone test, both of which are diagnostic blood tests that are commercially available. When the level of estrogen and/or testosterone falls below this level in an individual selected for HD (e.g., usually and optimally before recognition of any symptoms) or a trinucleotide repeat disorder, then an amount of estrogen and/or testosterone can be administered to keep the levels in this range.

Maintaining estrogen and/or testosterone levels in individuals having HD or a trinucleotide repeat disorder can be done by administering the estrogen/testosterone compound, as described herein, and can take the form of injection, transdermal patches and/or oral therapy.

Animal models of transgenic mice have been developed for the mutant HD gene and specifically it is known that these mice that carry this transgenic gene containing the first exon of the mutant HD gene and have the identical function as the human mutant HD gene. The brains of HD patients and animal models of HD have specific abnormalities that are negatively affected by deficiency of testosterone, estrogen, or their precursors. Abnormalities in monoamingeric neurotransmission are implicated in the disease process. HD pathogenesis suggests that an early excess of dopaminergic activity causes excitotoxic cell death that is followed by a dopaminergic deficiency as neuronal death ensues. Estrogen's, testosterone's, and their precursors' known anti-dopaminergic action in the striatum enables them to function early in the disease as neuroprotectants. A differential sensitivity to glutamate causes glutamate toxicity that, in turn, affects spiny neurons in the striatum. Expression of the huntingtin polyglutamine expansion in cells exposed to NMDA-type glutamate receptors causes increased excitotoxic cell death when compared to control cells. Estrogen, testosterone and/or their precursors act to suppress mRNA levels of certain NMDA-glutamate receptors and are thus able to protect neurons against glutamate toxicity. Estrogen, testosterone, and/or their precursors mediate neuroprotection in neurons induced to undergo apoptosis. Apoptosis, or programmed cell death, is generally used by multicellular organisms to eliminate unnecessary or dangerous cells. Apoptosis is normally important to the development of the brain and nervous system, the immune systems and various body tissues. However, in the case of HD, apoptosis leads to excessive degeneration of nerve cells. Apoptosis is induced by the mutant polyglutamine from the huntingtin protein, causing an influx of Ca+ into a cell through the glutamate receptor. Genes are typically essential for Programmed Cell Death (PCD) and, by blocking the expressed gene products, such as the HD gene product that codes for the huntingtin protein, PCD is inhibited. In this case, estrogen, testosterone and/or their precursors bind to the polyglutamine located on the end of the mutant huntingtin protein to prevent the protein from inducing cell death by preventing aggregate accumulation on the nuclear membrane and in the nuclei of these neurons. The ability of estrogen, testosterone, and their precursors to bind to the mutant huntingtin protein decreases as one ages because the production of estrogen, testosterone, and their precursors decreases with age. Since the length of the CAG polyglutamate repeat determines the level of hormone needed to render this protein ineffective in causing cell death, in an embodiment, it is an embodiment of the present invention, to begin treatment before ones natural reserves of hormone are depleted with age. The extent of treatment with estrogen, testosterone, and/or their precursors will depend on a given individual based on the length of the CAG glutamine repeat in that individual and the stage of the disease. Elevated monoamine oxidase (MAO) activity in the brain of HD patients is believed to be the basis for the depressive symptoms so often characteristic of HD. Estrogen, testosterone, and their precursors inhibit MAO activity and have an anti-depressant action. Estrogen's, testosterone's, and their precursors' ability to increase cerebral blood flow is believed to counter the decreased cerebral and caudate blood flow associated with HD. Estrogen, testosterone, and their precursors serve as brain protectants in this process. Following is a preferred method for determining the rate of estrogen binding based on the length of the CAG glutamine repeat. Comparable tests can then be used by physicians in a testing regimen in which hormone levels, such as estradiol levels, as well as the poly-glutamine repeat length of the individual are measured to determine the optimum time to begin therapy.

EXEMPLIFICATION

Example 1

In Vitro Studies Show that Estradiol Binds the Mutant Form of Huntingtin Protein Glycerol Bacterial stocks of three different CAG repeat lengths contained within the first exon of Huntington and cloned into the PGex vector 2T were used to inoculate overnight cultures of 25 Ml containing 50 mglmL ampicillin. Pgex is a glutathione transferase fusion expression system Amersham Cat#-27-4587-01-. This system allows for the efficient overproduction of a target protein along with the glutathione-S-transferase as a fusion. These cultures were previously grown and DNA preparations of each were made. They were then sequenced using dye terminator sequencing technique and run on an ABI 377 auto sequencer. The results show a 23 CAG repeat contained within the first exon of Huntingtin labeled Q23. A 47 CAG repeat contained within the first exon of Huntingtin labeled Q47 and a 63 CAG repeat contained within the first exon of Huntingtin labeled Q63. The bacterial culture used to make this DNA prep was divided in half. Half of it was used for the DNA prep (to specifically identify the number of CAG repeats using dyterminator DNA sequencing) and the other half was used to make the glycerol stock used to inoculate these cultures to produce over-expression of the proteins containing three variables of the CAG repeats. After overnight growth at 37 degrees, the cultures were diluted 1:100 (e.g. 1.25 mL into 125 ml of LB containing 50 mg/ml of antibiotic ampicillin) and then allowed to continue to grow into middle log phase 1.5 hours.

At this point, the bacterial cultures were made using 1.0 mM Isopropyl-b-dThiogalactopyranoside (IPTG) by diluting 100 mM IPTG 1:100 (1.25 mL of 100 mM IPTG into 125 ml of growth culture representing approximately 0.6 OD (optical density) at 590 nM using a common light spectrophotometer). These three cultures were then allowed to grow overnight (20 hrs.) at 30 degrees. These cultures were then centrifuged at 600 rpm for 30 minutes to collect the bacteria. The bacterial pellets were then transferred to a 1.5 mL conical centrifuge tube and 1.0 mL of ice cold PBS (phosphate buffed saline) was added and the pellets dissolved by vortexing for five minutes. This was then split into two 1.5 mL conical tubes containing 700 µL each for all three bacterial preps and then 350 µL of 3% N-lauyl sacosine was added to each of the six tubes, mixed, and then each tube was sonicated for a total of 30 seconds using a Fisher probe sonicator Model number F-50. Next the six tubes were centrifuged in a microfuge top speed for 10 minutes.

The bacterial supernatant of a rich brown color was added directly to the equivalent of 400 µL of Glutathione Sepharose 4B (strict affinity for the glutathione portion of the fusion-target protein over produced) beads washed with ten bead volumes of ice cold PBS. The bacterial supernatant, as a slurry with the Glutathione sepharose, was allowed to gently rock for 30 minutes. After the binding was complete, the bead slurry was centrifuged at 200 rpm 20 seconds to pellet the bead and then repetitively washed five times with two bead volumes with ice cold PBS. After the last supernatant was removed and discarded, the beads were subjected to elution with 10 mM reduced glutathione in 50 mM tris Ph 8.0 by allowing incubation for 10 minutes under gentle shaking.

These were then centrifuged 30 seconds at 200 rpm and the elute removed and saved to a new tube. Next, 20 µl of protease inhibitor was added PMSF. Then 30 µL of these were then subjected to polyacylamide gel electrophoresis (PAGE) 12% gels overnight at 90 volts constant voltage.

The next day the gels were stained with coomassie brilliant blue in 50% methanol and 10% acetic acid, for two hours at 50 degrees, and then further destained in the same solution composition minus the coomassie blue for up to four hours. The resultant image shows purification of all three mutant huntingtin protein bands.

These pure proteins were then used in the following binding protocol. Oestradiol-6-(0-carboxymethyl) oximino-(2-[125I] iodohistamine was used as the estradiol source. Buffer B preferably comprises: 250 mM tris, 150 mM NaCI, and a Dextran Charcoal solution comprising 0.05% Dextran coated charcoal in buffer B (sigma Cat#6197). About 0.5 ml of buffer B was preferably used per reaction. A total of 5 ml of Buffer B was aliquoted into a glass borosilicate tube (Fisher Cat #14-961-26) and 10 µL of Oestradiol (I125) was added containing approximately 2,000,000 cpm. About 0.5 ml of this solution was then distributed into eight labeled glass tubes (cat #14-961-260). The entire tube #1's 500 µL was counted. Tube #2 through #8 were treated in the following manner:

TABLE 1

| Tube #1 | Total cpm in 0.5 mL of cocktail |
| Tube #2 | zero/0.5 mL cocktail |
| Tube #3 | Q23/0.5 mL cocktail + 50 µL Eluate 1 |
| Tube #4 | Q23/0.5 mL cocktail + 50 µL Eluate 1 |
| Tube #5 | Q47/0.5 mL cocktail + 50 µL Eluate 3 |
| Tube #6 | Q47/0.5 mL cocktail + 50 µL Eluate 3 |
| Tube #7 | Q63/0.5 mL cocktail + 50 µL Eluate 5 |
| Tube #8 | Q63/0.5 mL cocktail + 50 µL Eluate 5 |

Tubes #2-#8 were incubated for 1 hour at room temperature, placed on ice for ten minutes, and 200 µL of the Dextran charcoal solution in buffer B was added. These tubes were then placed on ice ten minutes and then centrifuged 15 minutes at 2200 rpm in a Sorvall RC-3 refrigerated centrifuge with swinging bucket rotor (Sorvall HL-8) at 4 degrees. The entire 700 µL supernatant was removed and counted using Genesys multi-well gamma counter (Laboratories Technology, Inc.). The results are summarized below:

TABLE 2

| Counts per minute (cpm): | | |
| --- | --- | --- |
| Total: | 184,972 | (I 125) estradiol in buffer B (count entire tube) |
| Zero: | 27,388 | Charcoal Filtered, count supernatant only |
| Sample HD Q23: | 50,107 | +HD Q23, Charcoal Filtered, Count Sup. |
| Sample HD Q23: | 53,797 | +HD Q23, Charcoal Filtered, Count Sup. |
| Sample HD Q47: | 47,454 | +HD Q47, Charcoal Filtered, Count Sup. |
| Sample HD Q47: | 44,767 | +HD Q47, Charcoal Filtered, Count Sup. |
| Sample HD Q63: | 38,221 | +HD Q63, Charcoal Filtered, Count Sup. |
| Sample HD Q63: | 38,040 | +HD Q63, Charcoal Filtered, Count Sup. |

The significance of these data is that an affinity for estradiol has been demonstrated using the mutant form of huntingtin, the causative protein in Huntington's disease. It is therefore now applicable that Huntington Disease patients and their at-risk family members should have their polyglutamine repeat length tested and if recognized, to start on a regimen of estradiol, or related hormone, replacement therapy as soon as their normal level of these hormones drop below physiologic levels. Physicians set up a testing regimen that determine both estradiol levels as well as the poly-glutamine repeat length to determine the optimum time to begin therapy. It is thereby shown that estradiol is the limiting factor in the progression of Huntington's disease. The estradiol level, or the serum level of other applicable hormones, in conjunction with the known CAG repeat length of affected individuals, is therefore predictive of the symptomatic onset of Huntington's Disease and thus will establish the optimum time in the individual's life to begin administering the appropriate hormone therapy.

Example 2

In Vivo Treatment of HD Animals with Estrogen and Testosterone Administration

Summary:

HD is a neurodegenerative disorder caused by a CAG/polyglutamine repeat expansion. Mice have been generated that are transgenic for the 5' end of the human HD gene carrying CAG115-CAG160 repeat expansions. The most severe (CAG 158-160) repeat length was chosen for this study. Although there was the possibility that any treatment would be ineffective at this severity of disease state, even a minimal improvement in cognitive and motor function is suggestive of a treatment.

In this study that Estrogen and/or Testosterone treatment of transgenic mice, even at this severe induction of disease, provide a significant improvement in both cognitive decision making and motor function 14 days (16.6% improvement) after their untreated liter mates were unable to perform the trained task. Correlation of body and brain weights with these improvements in treated animals reveals a treatment for HD.

Specific Aim:

The specific aim of this study is to determine if Estradiol/Testosterone treatment of HD transgenic mice will delay or stop the onset of symptoms of HD.

Methods:

Thirty (30) hemizygous mice were tested to determine their ability to transverse a ½ inch square beam the distance of one meter. They were injected with estradiol cypionate (DEPO®-ESTRADIOL, Pfizer, Inc.) or testosterone cypionate (DEPO®-TESTOSTERONE, Pfizer, Inc.) as an emulsion with freunds incomplete adjuvant. Hormone tests of serum were performed to verify the blood levels of estradiol or testosterone. The mice (controls=no treatment) were tested against liter mates receiving either (E1 and E3 100 ug/ml weekly) or (E2 and E4 200 ug/ml injection weekly). The test will consist of Beam walking, (measuring coordination, slip falls and distance in a measured time interval), brain weight and body weight. The testing will be performed twice weekly from week 5 through week 12 of age.

Two groups of mice, 15 female and 15 male mice will be utilized.

30 HD mice were obtained from the Jackson Laboratory, Bar Harbor, Me. The group consists of a 15 hemizygous female strain #2810 and 15 hemizygous males strain #2810 (containing the transgene HDexon 1+159-161 CAG repeat units). These mice were grouped as follows:

All mice received ear clips as identification, noting hair color.
1-15 were males and 16-29 were females mouse #30 arrived dead.

Male mice: 1-4 were control animals receiving no treatment, 5, 6, 7, 11 were grouped as E1 8, 9, 10 and 12 were grouped as E2. 13, 14 and 15 were grouped as T1, receiving 100 ug/ml testosterone weekly.

Female mice: 16-19 were control animals receiving no treatment. 20, 21, 22, 26 were grouped as E3, 23, 24, 25, 27 were grouped as E4. 28 and 29 were grouped as T2, receiving 100 ug/ml testosterone. See table 3 for a summary.

TABLE 3

| | Male (M)/Female (F) | Estradiol (E)/Testosterone(T) | Amount received | Numeral Designation |
|---|---|---|---|---|
| E1 | M | E | 100 ug/ml | 5, 6, 7, 11 |
| E2 | M | E | 200 ug/ml | 8, 9, 10, 12 |
| E3 | F | E | 100 ug/ml | 20, 21, 22, 26 |
| E4 | F | E | 200 ug/ml | 23, 24, 25, 27 |
| T1 | M | T | 100 ug/ml | 13, 14, 15 |
| T2 | F | T | 100 ug/ml | 28, 29 |
| Control | M | None | None | 1-4 |
| Control | F | None | None | 16-19 |

Observations included behavioral testing and body weight selected to measure motor aspects of fore limb and hind limb coordination, balance, including raised beam. Blood specimens for estradiol assay using Elisa methodology was obtained during the study.

Estradiol/Testosterone Injection:

Stock solution of estradiol and testosterone were diluted with water and mixed with Freund's incomplete adjuvant. This was mixed continuously for 1 minute and either 100 ul (E1 and E3) or 200 ul (E2 and E4) were injected subcutaneously. Estrogen or testosterone release was continuous over six days. Peak measured levels were obtained in 24 hr as shown in previous studies. Animals in the E1 and E3 groups were targeted to receive 100-300 pg/ml estrogen and groups E2 and E4 were targeted to receive 400-800 pg/ml of estrogen. Animals in T1 and T2 grouping were targeted to receive 100 pg/ml testosterone.

Behavioral Testing:

Behavioral testing included beam walking, brain weight and body weight assessment.

Beam Walking:

Utilizing the raised beam, mice were assessed for their ability to transverse a graded series of narrow beams to reach a safety platform. The beams consisted of long strips of wood with a 12 mm or 5 mm square cross section. The beams were placed horizontally, 50 cm above each bench surface, with one end mounted on a narrow support and the other end attached to an enclosed box to which the animal could escape. Two inches of dense foam was placed under the test area to protect the animals from fall injury. Training took place in a 3 or 4 day period, where the mice were trained two to four times in a four day period using the 12 mm square beam. Once they were trained to walk the beam (i.e., traversing the 12 mm square beam in less than 20 seconds), they received two consecutive trails on each of the square beam and each of the round beams, in each case progressing from the widest to the narrowest beam. Mice were afforded 150 seconds to traverse each beam. The number of times the mice slipped off of the beam was recorded for each trial. The mean score was used for each trial.

Body Weight: All animals were weighed on a scale weekly throughout the study. All weights were recorded.

After euthanized, all brains of all mice were surgically removed and placed in a solution of formaldehyde and weighed on a scale. The weights were recorded.

Results:

A significant improvement was found in the ability of the estrogen and testosterone treated animal to transverse the narrowest beam, a beam that was ½ square inches. In motor skill, both hind limb and forelimb coordination were statically improved over their liter mate control subjects as was shown by their ability to transverse the ½ in² beam. The mean average of CAG repeat length was 159.60, mice severely affected with HD. Two weeks after the control animals were unable to transverse even one fourth of the beam, the estrogen/testosterone treated animals continued to be able to cross the ½ in² beam under the time allotted (a 16.6% improvement over the course of this study). These observations of coordination and control of muscle movement further show the therapeutic effects of estrogen and testosterone treatment of Huntington diseased mice. Additionally, treated mice retained their body weight significantly better than non-treated mice. Table 4 shows the direct correlation of hormone treated (estrogen and/or testosterone) mice and their body weight retention, which is directly related to their ability to perform motor function tests.

Table 4 shows the direct correlation of hormone treatment with body weight in female mice. The average number of CAG repeat for all mice was 159.60.

TABLE 4

| Females ID # | Peak wt Weeks 8/9 | Last wt Week 12 | Change in Grams | % change in weight | Average % change | ES/TT pg/ml |
|---|---|---|---|---|---|---|
| C, 16 | 18.4 g | 13.5 g | −4.9g | −26.6% | 21.7% | 12.2 pg/ml |
| C, 17 | 23.5 g | 19.1 g | −4.4g | −18.7% | 21.7% | 27.9 pg/ml |
| C, 18 | 20.5 g | 17.7 g | −2.8g | −13.6% | 21.7% | 17.1 pg/ml |
| C, 19 | 22.1 g | 15.9 g | −6.2g | −28.0% | 21.7% | 26.1 pg/ml |
| E1, 20 | 25.0 g | 18.2 g | −6.8g | −27.2% | 15.5% | 49.8 pg/ml |
| E1, 21 | 24.0 g* | 21.7 g | −2.3g | −9.0% | 15.5% | 261.5 pg/ml |
| E1, 22 | 19.9 g | 16.9 g | −3.0g | −15.0% | 15.5% | 371.9 pg/ml |
| E1, 26 | 21.2 g | 18.9 g | −2.3g | −10.8% | 15.5% | 258.3 pg/ml |
| E2, 23 | 21.5 g* | 20.5 g | −1.0g | −4.6% | 15.7% | 902.9 pg/ml |
| E2, 24 | 21.8 g | 17.6 g | −4.2g | −19.2% | 15.7% | 651.2 pg/ml |
| E2, 25 | 19.8 g | 13.5 g | −6.3g | −31.0% | 15.7% | Dead |
| E2, 27 | 22.5 g | 20.7 g | −1.8g | −8.0% | 15.7% | 20.4 pg/ml |
| T1, 28 | 27.6 g | 17.4 g | −10.2g | −36.9% | 34.8% | 647.0 pg/ml |
| T1, 29 | 21.6 g | 14.5 g | −7.1g | −32.8% | 34.8% | — |

Table 5 shows a direct correlation between hormone treatment and body weight in male mice. All mice had an average CAG repeat of 159.60

TABLE 5

| Males ID# | Peak wt Weeks 8/9 | Last wt Week 12 | Change in Grams | % change | Average % Change | ES/TT pg/ml |
|---|---|---|---|---|---|---|
| C, 1 | 25.9 g | 18.4 g | −7.5 g | −28.9% | 27.2% | 15.6 pg/ml |
| C, 2 | 29.0 g | 20.2 g | −8.8 g | −30.0% | 27.2% | — |
| C, 3 | 23.4 g | 18.7 g | −4.7 g | −20.0% | 27.2% | 28.1 pg/ml |
| C, 4 | 26.0 g | 18.2 g | −7.8 g | −30.0% | 27.2% | 14.1 pg/ml |
| E3, 5 | 26.4 g | 23.5 g | −2.9 g | −10.9% | 15.9% | 317.7 pg/ml |
| E3, 6 | 26.2 g | 19.6 g | −6.6 g | −25.0% | 15.9% | 443.5 pg/ml |
| E3, 7 | 26.7 g | 22.6 g | −4.1 g | −15.3% | 15.9% | 316.9 pg/ml |
| E3, 11 | 24.8 g | 21.7 g | −3.1 g | −12.5% | 15.9% | 555.9 pg/ml |
| E4, 8 | 26.2 g | 22.9 g | −3.3 g | −12.5% | 14.9% | 586.6 pg/ml |
| E4, 9 | 24.6 g | 19.6 g | −5.0 g | −20.3% | 14.9% | — |
| E4, 10 | 23.7 g | 20.2 g | −3.5 g | −14.7% | 14.9% | 388.1 pg/ml |
| E4, 12 | 22.1 g | 19.4 g | −2.7 g | −12.2% | 14.9% | 1,297 pg/ml |
| T2, 13 | 23.4 g | 17.1 g | −6.3 g | −26.9% | 22.2% | 468.1 pg/ml |
| T2, 14 | 28.0 g | 25.1 g | −2.9 g | −10.3% | 22.2% | 937.7 pg/ml |
| T2, 15 | 27.0 g | 19.0 g | −8.0 g | −29.6% | 22.2% | 1,494 pg/ml |

C = control animals, no treatment

TABLE 5-continued

| Males ID# | Peak wt Weeks 8/9 | Last wt Week 12 | Change in Grams | % change | Average % Change | ES/TT pg/ml |
|---|---|---|---|---|---|---|

E1, E3 = 100 ul ES dose-target blood level-100-300 pg/ml
E2, E4 = 200 ul ES dose-target blood level-400-800 pg/ml
T1, T2 = 100 ul T dose-target blood level-50-100 pg/ml Control animals lost on average 21.7% of their peak body weight (females) as compared to their treated liter mates, who lost an average of (E1) 15.5% and (E2) 15.7% weight loss. The male treated animal had similar findings. The control animals lost on average 27.2% of their peak body weight as compared to treated mice who had experienced a (E3) 15.9% and (E4) 14.9% weight loss. Weight loss is a significant symptom of HD and usually attributed to mid onset of the diseased state.

Referring to the E1, Female ID #20, a sample from this particular mouse indicated that only about 49.8 pg/ml of estrogen was present, as compared to other mice in the same group with 5 to 7 times that amount. For whatever reason, the mouse did not absorb the requisite or desired amount of estrogen and accordingly, the mouse lost 27.2% of its body weight as compared to other members of the same group that only lost an between 4.6% and 15% of their body weight. This difference in body weight in light of the amount of estrogen absorbed is clear evidence that estrogen administration/absorption directly correlates with weight loss prevention, one of the most important symptoms of HD.

The treated animals were better able to make decisions and coordinated their forelimb and hind limb motor movements to cross the ½ in² beam without significant hesitation and within the time allotted. None of the control (untreated) animals were able to coordinate their decision making and motor function to cross the beam in the allotted time after week 10. Furthermore, if left for a longer duration of time (data not shown), the control animals just stayed on the start platform unable (or willing) to move.

Table 6 shows the correlation between treated/untreated, CAG repeat length and brain weight. On average the lower level (100-300 Pg/ml) of estrogen treatment showed up to a 10% increase in brain weight.

TABLE 6

| Animal ID# | Brain weight at week 12 | CAG repeat length |
|---|---|---|
| C, 1 | 0.36 g | 163 |
| C, 2 | — | 159 |
| C, 3 | 0.36 g | 160 |
| C, 4 | 0.23 g | 161 |
| E3, 5 | 0.40 g | 159 |
| E3, 6 | 0.37 g | 159 |
| E3, 7 | 0.37 g | 160 |
| E4, 8 | 0.39 g | 158 |
| E4, 9 | — | 159 |
| E4, 10 | 0.34 g | 159 |
| E3, 11 | 0.40 g | 158 |
| E4, 12 | 0.35 g | 160 |
| T2, 13 | 0.31 g | 159 |
| T2, 14 | 0.37 g | 159 |
| T2, 15 | 0.33 g | 161 |
| C, 16 | 0.32 g | 160 |
| C, 17 | 0.35 g | 160 |
| C, 18 | 0.33 g | 158 |
| C, 19 | 0.33 g | 160 |
| E1, 20 | 0.33 g | 159 |
| E1, 21 | 0.36 g | 161 |
| E1, 22 | 0.34 g | 159 |
| E2, 23 | 0.33 g | 158 |
| E2, 24 | 0.37 g | 162 |

TABLE 6-continued

| Animal ID# | Brain weight at week 12 | CAG repeat length |
|---|---|---|
| E2, 25 | — | 162 |
| E1, 26 | 0.30 g | 158 |
| E2, 27 | 0.37 g | 159 |
| T1, 28 | 0.31 g | 159 |
| T1, 29 | — | 160 |

FIG. 1 shows the combined data of six mice, 3 controls and both estrogen levels in 2 male and 1 female mice. All control animals were unable to complete the task of traversing the ½ in. beam in 150 seconds, whereas all of the treated animals shown were able to complete the traversing of the beam in the allotted time shown.

FIGS. 2A, 2B, 3A, 3B, and 4A, 4B show the data comparing one control mouse to one treated animal. In all cases shown the treated animals demonstrated a significant increase in their ability to cross the beam within the time allotment. Additionally the data show the ability of the treated animals to completely transverse the beam as measured by distance. The untreated control animals were unable to cross even the shortest distance after week 10.

Although specific features of the invention are described in connection with some of the preferred methods and not others, this is for convenience only as some feature may be combined with any or all of the other features in accordance with the invention. Other embodiments will occur to those skilled in the art and are within the following claims.

The relevant teachings of all the references, patents and/or patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating a female individual having Huntington's Disease (HD) or a female individual having an HD gene having a number of CAG repeats greater than or equal to about 36; the method comprising:
    a. selecting a female individual having HD or an HD gene having a number of CAG repeats greater than or equal to about 36;
    b. administering to the female individual an amount of 17β-estradiol, wherein the amount of administration to the female individual ranges from about 0.2 mg to about 10 mg;
        wherein the individual with HD or HD gene having a number of CAG repeats greater than or equal to about 36 is treated.

2. The method of claim 1, further comprising measuring levels of 17β-estradiol in the female individual.

3. The method of claim 1, wherein the female individual has greater than 40 CAG repeats.

4. The method of claim 1, wherein the female individual has between about 36 and about 120 CAG repeats.

5. The method of claim 1, wherein one or more symptoms of HD is reduced, wherein the symptoms of HD comprise weight loss, loss of fine motor function, loss of gross motor function, a loss in cognitive function, chorea, loss of brain tissue, or a combination thereof.

6. The method of claim 5, wherein one or more of the symptoms are reduced by between about 5% and about 100%.

7. The method of claim 5, wherein the Unified Huntington's Disease Rating Scale (UHDRS) score remains about the same or does not increase.

8. The method of claim 5, wherein one or more of the symptoms are reduced by between about 5% and about 100%.

9. The method of claim 5, wherein the Unified Huntington's Disease Rating Scale (UHDRS) score remains about the same or does not increase.

10. The method of claim 1, wherein selecting a female individual having HD comprises assessing the presence or absence of a mutant HD gene having between about 36 and 120 CAG repeats.

11. The method of claim 1, further comprising measuring levels of testosterone in the male individual.

12. The method of claim 1, wherein the male individual has greater than 40 CAG repeats.

13. The method of claim 1, wherein the male individual has between about 36 and about 120 CAG repeats.

14. The method of claim 1, wherein one or more symptoms of HD is reduced, wherein the symptoms of HD comprise weight loss, loss of fine motor function, loss of gross motor function, a loss in cognitive function, chorea, loss of brain tissue, or a combination thereof.

15. The method of claim 1, wherein selecting male individual having HD comprises assessing the presence or absence of a mutant HD gene having between about 36 and 120 CAG repeats.

16. A method of reducing one or more symptoms associated with HD in an individual, wherein the method comprises:
    a. selecting the individual having HD; and
    b. administering to the individual an amount of 17β-estradiol or testosterone, wherein the amount of administration to an individual ranges from about 0.2 mg to about 10 mg of 17β-estradiol for a female individual or about 1 mg to about 35 g of testosterone for a male individual; wherein one or more symptoms associated with HD in the individual are reduced, as compared to the same in an individual with HD not subjected to step b.

17. The method of claim 16, wherein the symptoms of HD comprise weight loss, loss of fine motor function, loss of gross motor function, a loss in cognitive function, chorea, loss of brain tissue, or a combination thereof.

18. The method of claim 17, wherein one or more symptoms are reduced by an amount between about 5% and about 100%.

19. A method of preventing weight loss, or reducing the amount of weight loss in an individual having HD, wherein the method comprises:
    a. selecting the individual having HD; and
    b. administering to the individual an amount of 17β-estradiol or testosterone, wherein the amount of administration to the individual ranges from about 0.2 mg to about 10 mg of 17β-estradiol for a female individual or about 1 mg to about 35 g of testosterone for a male individual; wherein weight loss is prevented or the amount of weight loss is reduced in the individual with HD, as compared to an individual with HD not subjected to step b.

20. The method of claim 19, wherein the amount of weight loss is reduced by between about 5% and about 100%.

21. The method of claim 19, wherein selecting the individual having HD comprises assessing for the presence or absence of a mutant huntingtin protein having a polyglutamine tract, or a mutant HD gene having a CAG repeat.

22. A method of treating an individual having HD, the method comprising:

a. assessing the individual for the presence or absence of HD or for the presence or absence of an HD gene having a number of CAG repeats between about 36 and about 120;
b. assessing one or more levels of 17β-estradiol or testosterone in the individual to determine if the one or more levels is below a normal level; and
c. administering to the individual an amount of 17β-estradiol or testosterone to maintain an average amount of 17β-estradiol or testosterone at a level between about 100 pg/ml to about 185 pg/ml of 17β-estradiol in a female individual, between about 20 pg/ml to about 40 pg/ml of free testosterone in a male individual, or between about 300 ng/dL and about 900 ng/dL of total testosterone in a male individual.

23. The method of claim 22, wherein the 17β-estradiol or testosterone is administered periodically, daily, or weekly.

24. A method of modifying activity of a mutant huntingtin protein in an individual having HD such that one or more symptoms of HD are reduced, wherein the method comprises:
administering to the individual an amount of 17β-estradiol or testosterone;
wherein the activity of the mutant huntingtin protein is modified and one or more symptoms of HD are reduced, as compared to the same in an individual with HD not subjected to the administration step.

25. The method of claim 24, wherein 17β-estradiol binds to the mutant huntingtin protein.

26. The method of claim 24, further including assessing the presence or absence of the mutant huntingtin protein or of an HD gene having greater than or equal to 36 CAG repeats.

27. A method of treating an individual having HD, the method comprising:
a. assessing an individual for the presence or absence of HD or for the presence or absence of an HD gene having a number of CAG repeats between about 36 and about 120 to thereby obtain an individual with HD;
b. assessing an average level of 17β-estradiol in the individual to determine if the level of 17β-estradiol is below about 100 pg/ml;
c. administering to the individual having HD and a level of 17β-estradiol below about 100 pg/ml, an amount of 17β-estradiol, wherein the amount of administration to the individual ranges from about 0.2 mg to about 10 mg; wherein the individual with HD is treated.

28. A method of delaying symptoms of Huntington's Disease (HD) in an individual having a number of CAG repeats greater than or equal to about 36; the method comprising:
d. selecting an individual having an HD gene having a number of CAG repeats greater than or equal to about 36;
e. administering to the individual an amount of 17β-estradiol or testosterone, wherein the amount of administration to the individual ranges from about 0.2 mg to about 10 mg of 17β-estradiol for a female individual or about 1 mg to about 35 g of testosterone for a male individual;
wherein the individual with HD gene having a number of CAG repeats greater than or equal to about 36 has a delayed onset of symptoms of HD compared to the onset of symptoms of HD in an individual not administered an amount of 17β-estradiol or testosterone, wherein the symptoms of HD comprise weight loss, loss of fine motor function, loss of gross motor function, a loss in cognitive function, chorea, or loss of brain tissue, or a combination thereof.

29. A method of treating an individual having Huntington's Disease (HD) or an individual having an HD gene having a number of CAG repeats greater than or equal to about 36; the method comprising:
f. selecting an individual having HD or an HD gene having a number of CAG repeats greater than or equal to about 36;
g. administering to the individual a compound that results in administration of an amount of 17β-estradiol, wherein the amount of administration of the compound to the individual ranges from about 0.2 mg to about 10 mg;
wherein the individual with HD or HD gene having a number of CAG repeats greater than or equal to about 36 is treated.

30. A method of treating a male individual having Huntington's Disease (HD) or a male individual having an HD gene having a number of CAG repeats greater than or equal to about 36; the method comprising:
a. selecting a male individual having HD or an HD gene having a number of CAG repeats greater than or equal to about 36; and
b. administering to the male individual an amount of testosterone, wherein the amount of administration to the male individual ranges from about 1 mg to about 35 g,
wherein the individual with HD or HD gene having a number of CAG repeats greater than or equal to about 36 is treated.

31. A method of treating a male individual having HD, the method comprising:
a. assessing a male individual for the presence or absence of HD or for the presence or absence of an HD gene having a number of CAG repeats between about 36 and about 120 to thereby obtain a male individual with HD;
b. assessing one or more levels of testosterone in the male individual to determine if the level of free testosterone is below about 20 pg/ml, or the level of total testosterone is below about 300 ng/dL; and
c. administering to the male individual having HD and a level of free testosterone below about 20 pg/ml or a level of total testosterone below about 300 ng/dL, an amount of testosterone, wherein the amount of administration to a male individual ranges from about 1 mg to about 35 g; wherein the male individual with HD is treated.

* * * * *